(12) United States Patent
Ferreira Dos Santos Da Fonseca et al.

(10) Patent No.: US 11,534,568 B2
(45) Date of Patent: Dec. 27, 2022

(54) PRESSURE SUPPORT SYSTEM AND METHOD OF PROVIDING PRESSURE SUPPORT THERAPY TO A PATIENT

(71) Applicant: KONINKLIJKE PHILIPS N.V., Eindhoven (NL)

(72) Inventors: Pedro Miguel Ferreira Dos Santos Da Fonseca, Borgerhout (BE); Joyce Van Zanten, Waalre (NL); Tim Elisabeth Joseph Weysen, Maastricht (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 821 days.

(21) Appl. No.: 16/454,559

(22) Filed: Jun. 27, 2019

(65) Prior Publication Data
US 2020/0001038 A1 Jan. 2, 2020

Related U.S. Application Data

(60) Provisional application No. 62/691,322, filed on Jun. 28, 2018.

(51) Int. Cl.
*A61M 16/00* (2006.01)
*A61M 16/10* (2006.01)
(Continued)

(52) U.S. Cl.
CPC .... *A61M 16/1075* (2013.01); *A61M 16/0066* (2013.01); *A61M 16/024* (2017.08);
(Continued)

(58) Field of Classification Search
CPC ............ A61M 16/1075; A61M 16/024; A61M 16/0066; A61M 16/06; A61M 2205/3306;
(Continued)

(56) References Cited

U.S. PATENT DOCUMENTS

| 5,148,802 A | 9/1992 | Sanders |
| 5,313,937 A | 5/1994 | Zdrojkowski |

(Continued)

FOREIGN PATENT DOCUMENTS

| WO | 2010090509 A1 | 8/2010 |
| WO | 2015035315 A2 | 3/2015 |
| WO | 2015092627 A1 | 6/2015 |

OTHER PUBLICATIONS

Enrique A. Gil, Xavier L. Aubert, Domien G.M. Beersma, "Ambulatory estimation of human circadian phase using models of varying complexity based on non-invasive signal modalities", Annual International Conference of the IEEE Engineering in Medicine and Biology Society (EMBC), vol. 2014 2014, pp. 2278-2281).

(Continued)

*Primary Examiner* — Steven O Douglas

(57) ABSTRACT

A pressure support system for providing pressure support therapy to a patient, the pressure support device includes an airflow generator structured to generate a flow of breathing gas to the patient, a temperature conditioning unit structured to adjust a temperature of the breathing gas provided to the patient, and a processing unit structured to estimate a core body temperature of the patient for selected times of day based on one or more inputs and to control the temperature conditioning unit to adjust temperature of the breathing provided to the patient at the selected times of day based on the estimated core body temperatures of the patient.

20 Claims, 5 Drawing Sheets

(51) Int. Cl.
*A61M 16/06* (2006.01)
*A61B 5/11* (2006.01)
*A61B 5/00* (2006.01)

(52) U.S. Cl.
CPC .............. *A61M 16/06* (2013.01); *A61B 5/1102* (2013.01); *A61B 5/4857* (2013.01); *A61B 5/6892* (2013.01); *A61M 2205/3306* (2013.01); *A61M 2205/3606* (2013.01); *A61M 2205/3653* (2013.01); *A61M 2230/06* (2013.01); *A61M 2230/50* (2013.01); *A61M 2230/63* (2013.01)

(58) Field of Classification Search
CPC .. A61M 2205/3606; A61M 2205/3653; A61M 2230/06; A61M 2230/50; A61M 2230/63; A61B 5/1102; A61B 5/4857; A61B 5/6892
See application file for complete search history.

(56) References Cited

U.S. PATENT DOCUMENTS

| | | | |
|---|---|---|---|
| 5,433,193 A | 7/1995 | Sanders | |
| 5,632,269 A | 5/1997 | Zdrojkowski | |
| 5,803,065 A | 9/1998 | Zdrojkowski | |
| 6,029,664 A | 2/2000 | Zdrojkowski | |
| 6,457,472 B1 * | 10/2002 | Schwartz | A61M 16/0465 128/207.14 |
| 6,539,940 B2 | 4/2003 | Zdrojkowski | |
| 6,626,175 B2 | 9/2003 | Jafari | |
| 7,011,091 B2 | 3/2006 | Hill | |
| 7,299,090 B2 | 11/2007 | Koch | |
| 2004/0158303 A1 | 8/2004 | Lennox | |
| 2015/0040905 A1 * | 2/2015 | Kulstad | A61M 16/10 128/204.23 |
| 2018/0364109 A1 | 12/2018 | Bongers | |

OTHER PUBLICATIONS

Kurt Krauchi and Tom Deboer, Body Temperatures, Sleep, and Hibernation, Chapter 28, pp. 323-334.

Kazue Okamoto-Mizuno and Kkoh Mizuno, "Effects of thermal environment on sleep and circadian rhythm", Journal of Physiological Anthropology, pp. 1-9, 2012.

Kei-Ichiro Kitamura, Xin Zhu, Wenxi Chen and Tetsu Nemoto, "Development of a new method for noninvasive measurement of deep body temperature wit hout a heater", Medical Engineering & Physics 32, pp. 1-6, 2010.

Hanns-Chritian Gunga, Mariann Sandsund, Randi E. Reinertsen, Frank Sattler & Jochim Koch, "A noninvasive device to continuously determine heat strain in humans", Journal of Thermal Biology 33, pp. 297-307, 2008.

* cited by examiner

PRESSURE SUPPORT SYSTEM AND METHOD OF PROVIDING PRESSURE SUPPORT THERAPY TO A PATIENT

BACKGROUND OF THE INVENTION

1. Field of the Invention

The present invention pertains to a pressure support system, and, in particular, to a pressure support system that adjusts breathing gas temperature to a patient based on an estimated core body temperature.

2. Description of the Related Art

Many individuals suffer from disordered breathing during sleep. Sleep apnea is a common example of such sleep disordered breathing suffered by millions of people throughout the world. One type of sleep apnea is obstructive sleep apnea (OSA), which is a condition in which sleep is repeatedly interrupted by an inability to breathe due to an obstruction of the airway; typically the upper airway or pharyngeal area. Obstruction of the airway is generally believed to be due, at least in part, to a general relaxation of the muscles which stabilize the upper airway segment, thereby allowing the tissues to collapse the airway. Another type of sleep apnea syndrome is a central apnea, which is a cessation of respiration due to the absence of respiratory signals from the brain's respiratory center. An apnea condition, whether OSA, central, or mixed, which is a combination of OSA and central, is defined as the complete or near cessation of breathing, for example a 90% or greater reduction in peak respiratory air-flow.

Those afflicted with sleep apnea experience sleep fragmentation and complete or nearly complete cessation of ventilation intermittently during sleep with potentially severe degrees of oxyhemoglobin desaturation. These symptoms may be translated clinically into extreme daytime sleepiness, cardiac arrhythmias, pulmonary-artery hypertension, congestive heart failure and/or cognitive dysfunction. Other consequences of sleep apnea include right ventricular dysfunction, carbon dioxide retention during wakefulness, as well as during sleep, and continuous reduced arterial oxygen tension. Sleep apnea sufferers may be at risk for excessive mortality from these factors as well as by an elevated risk for accidents while driving and/or operating potentially dangerous equipment.

Even if a patient does not suffer from a complete or nearly complete obstruction of the airway, it is also known that adverse effects, such as arousals from sleep, can occur where there is only a partial obstruction of the airway. Partial obstruction of the airway typically results in shallow breathing referred to as a hypopnea. A hypopnea is typically defined as a 50% or greater reduction in the peak respiratory air-flow followed by oxyhemoglobin desaturation and/or a cortical arousal. Other types of sleep disordered breathing include, without limitation, upper airway resistance syndrome (UARS) and vibration of the airway, such as vibration of the pharyngeal wall, commonly referred to as snoring.

It is well known to treat sleep disordered breathing by applying a positive airway pressure (PAP) to the patient's airway using an airway pressure support system that typically includes a mask, a pressure generating device, and a conduit to deliver positive pressure breathing gas from the pressure generating device to the patient through the mask. This positive pressure effectively "splints" the airway, thereby maintaining an open passage to the lungs. In one type of PAP therapy, known as continuous positive airway pressure (CPAP), the pressure of gas delivered to the patient is constant throughout the patient's breathing cycle. It is also known to provide a positive pressure therapy in which the pressure of gas delivered to the patient varies with the patient's breathing cycle, or varies with the patient's effort, to increase the comfort to the patient. This pressure support technique is referred to as bi-level pressure support, in which the inspiratory positive airway pressure (IPAP) delivered to the patient is higher than the expiratory positive airway pressure (EPAP). It is further known to provide a positive pressure therapy in which the pressure is automatically adjusted based on the detected conditions of the patient, such as whether the patient is experiencing an apnea and/or hypopnea. This pressure support technique is referred to as an auto-titration type of pressure support, because the pressure support device seeks to provide a pressure to the patient that is only as high as necessary to treat the disordered breathing.

Pressure support therapies as just described involve the placement of a patient interface device including a mask component having a soft, flexible sealing cushion on the face of the patient. The mask component may be, without limitation, a nasal mask that covers the patient's nose, a nasal/oral mask that covers the patient's nose and mouth, or a full face mask that covers the patient's face. Such patient interface devices may also employ other patient contacting components, such as forehead supports, cheek pads and chin pads. The patient interface device is typically secured to the patient's head by a headgear component. The patient interface device is connected to a gas delivery tube or conduit and interfaces the pressure support device with the airway of the patient, so that a flow of breathing gas can be delivered from the pressure/flow generating device to the airway of the patient.

It is important that pressure support therapy is comfortable for a patient. Uncomfortable pressure support therapy can dissuade a patient from continuing with the therapy. For example, a patient may be very compliant with PAP therapy, but has the feeling that when he wakes up he does not feel good or does not feel refreshed. This patient may suspect that the therapy is either not working, or somehow negatively influencing their sleep. Another example is a non-compliant patient. Non-compliance may be due to many reasons, one of which arising from the disbelief by the patient that the therapy works for him/her, despite the information from the referring physician. Each time he uses the PAP therapy, he has the feeling that he sleeps worse than when not using it and therefore refuses to continue with a regular therapy.

Thermal intervention, either applied passively or actively by physical exercise, induces significant changes in skin temperatures and core body temperature (CBT). Not only is the intensity of a thermal intervention crucial, but also the skin region selected and the timing/duration of application. Furthermore, CBT and skin temperatures are very sensitive to changes in environmental temperature. Maximal total sleep time (TST) is found in the thermoneutral zone (the range of ambient temperature at which temperature regulation is achieved solely by vasomotor responses), and REM and slow-wave sleep have been shown to be vulnerable to thermal interventions. Thermal interventions may induce arousals and awakenings, which in turn can have thermoregulatory effects, for example, by elevating CBT. When a thermal load is given repeatedly, the thermoregulatory system can adapt and the effects on sleep are changed. For example, the arousing effects are reduced.

Pressure support therapy can cause a thermal intervention for a patient that causes discomfort and may induce arousals and awakenings.

SUMMARY OF THE INVENTION

A pressure support system for providing pressure support therapy to a patient, the pressure support device comprises: an airflow generator structured to generate a flow of breathing gas to the patient; a temperature conditioning unit structured to adjust a temperature of the breathing gas provided to the patient; and a processing unit structured to estimate a core body temperature of the patient for selected times of day based on one or more inputs and to control the temperature conditioning unit to adjust temperature of the breathing provided to the patient at the selected times of day based on the estimated core body temperatures of the patient.

A method of providing pressure support therapy to a patient comprises: generating a flow of breathing gas to the patient; receiving one or more inputs; estimating a core body temperature of the patient for selected times of day based on the one or more inputs; and adjusting a temperature of the breathing gas provided to the patient at the selected times of day based on the estimated core body temperatures of the patient.

A non-transitory computer readable medium storing one or more programs, including instructions, which when executed by a computer, causes the computer to perform a method of providing pressure support therapy to a patient. The method comprises: generating a flow of breathing gas to the patient; receiving one or more inputs; estimating a core body temperature of the patient for selected times of day based on the one or more inputs; and adjusting a temperature of the breathing gas provided to the patient at the selected times of day based on the estimated core body temperatures of the patient.

DETAILED DESCRIPTION OF EXEMPLARY EMBODIMENTS

Figure 1:
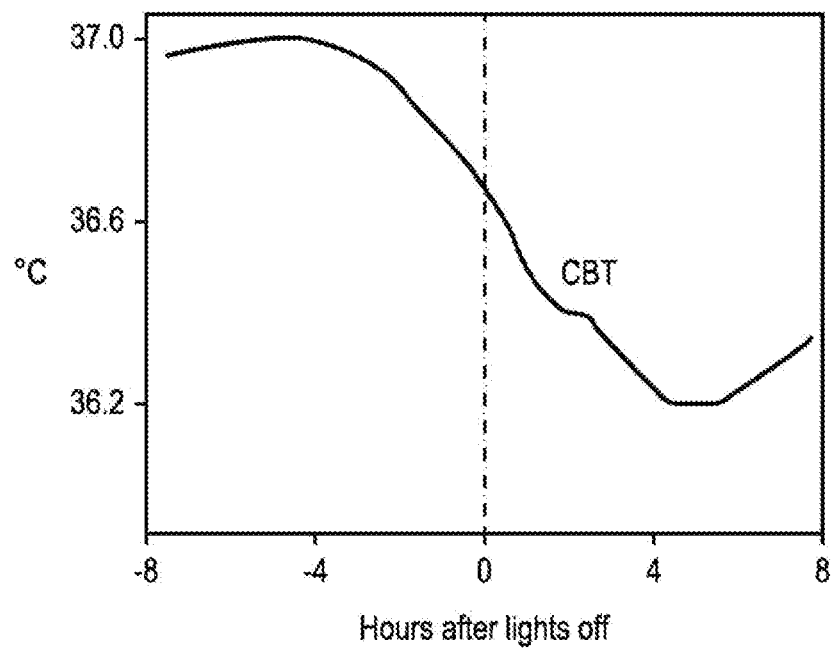
FIG. 1 is a graph showing a CBT of a patient before and during sleep according to an exemplary embodiment of the disclosed concept.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Breathing gas provided in pressure support therapy is typically provided at a constant temperature. While the temperature of the breathing gas may be comfortable at one time of day (i.e., one time of a 24-hour cycle), the temperature of the breathing gas may not be comfortable to the patient at another time of the day. For example, the temperature of the breathing gas may be comfortable during the evening, but may become uncomfortable later at points between midnight and morning.

FIG. 1 is a graph showing a CBT of a patient before and during sleep. In the graph, the hours after lights out indicates the approximate time the patient went to sleep. For example, 0 hours after lights out indicates the approximate time when the patient went to sleep and 4 hours after lights out is 4 hours after the approximate time the patient went to sleep. As shown in FIG. 1, the CBT of the patient drops to a low point about 5 hours after he has fallen asleep and then begins to rise again.

Breathing gas provided at a constant temperature to the patient during the beginning of his sleeping period may initially be comfortable to the patient, but may become uncomfortable to the patient in the middle of his sleeping period because the difference between the temperature of the breathing gas and the patient's CBT has changed due to the patient's CBT dropping during the sleep period. Even though the temperature of the breathing gas has remained the same, the breathing gas can cause a thermal intervention and discomfort because the patient's CBT has changed. The mismatch will vary through the night and can negatively influence sleep onset, sleep maintenance, and sleep continuity. The temperature of the conduit that provides breathing gas to the patient can also cause discomfort if it contacts the patient's skin during the night. The mismatch between the breathing gas or conduit temperature and the patient's CBT changing through the night can disrupt sleep continuity, increase sleep fragmentation, and lead to morning/daytime complaints of fatigue.

Thermoregulation in humans is primarily controlled by the circadian rhythm and by sleep regulation. Humans have a sleep-wake rhythm that is repeated approximately in a 24-hour cycle. The CBT decreases during the sleep phase and increases during the wake phase repeatedly according to the circadian rhythm. According to some exemplary embodiments of the disclosed concept, the temperature of breathing gas provided to a patient is adjusted based on an estimated core body temperature of the patient.

Figure 2:
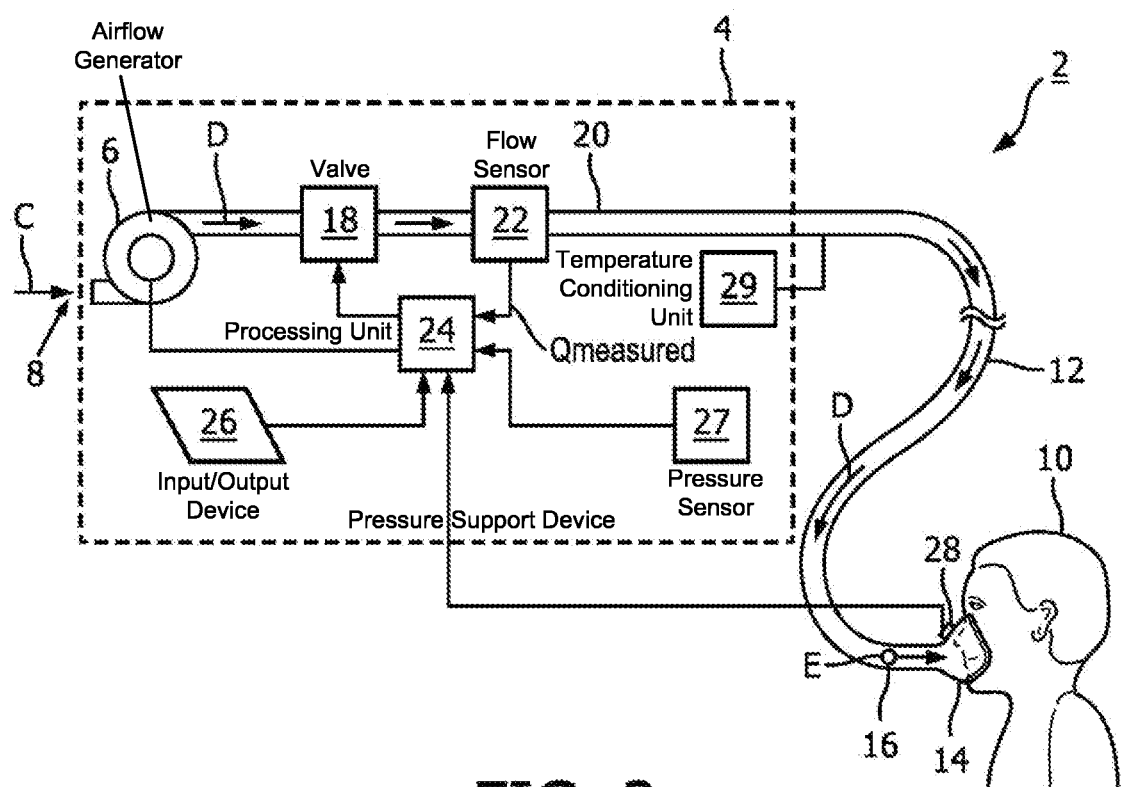
FIG. 2 is a schematic diagram of an airway pressure support system according to an exemplary embodiment of the disclosed concept.

FIG. 2 is a schematic diagram of an airway pressure support system 2 according to one particular, non-limiting exemplary embodiment in which the present invention may be implemented. Referring to FIG. 2, airway pressure support system 2 includes a pressure support device 4 which houses an airflow generator 6, such as a blower used in a conventional CPAP or bi-level pressure support device. Pressure generator 6 receives breathing gas, generally indicated by arrow C, from the ambient atmosphere through a filtered air inlet 8 provided as part of pressure support device 4, and generates a flow of breathing gas therefrom for delivery to an airway of a patient 10 at relatively higher and lower pressures, i.e., generally equal to or above ambient atmospheric pressure, to generate pressure to provide pressure compensation to patient 10 via a patient circuit 12,14. In the exemplary embodiment, airflow generator 6 is capable of providing a flow of breathing gas ranging in pressure from 3-30 cmH2O. The pressurized flow of breathing gas from airflow generator 6, generally indicated by arrow D, is delivered via a delivery conduit 12 to a breathing mask or patient interface 14 of any known construction, which is typically worn by or otherwise attached to patient 10 to communicate the flow of breathing gas to the airway of patient 10. Delivery conduit 12 and patient interface device 14 are typically collectively referred to as the patient circuit.

Pressure support system 2 shown in FIG. 2 is what is known as a single-limb system, meaning that the patient circuit includes only delivery conduit 12 connecting patient 10 to pressure support system 2. As such, an exhaust vent 16 is provided in delivery conduit 12 for venting exhaled gases from the system as indicated by arrow E. It should be noted that exhaust vent 16 can be provided at other locations in addition to or instead of in delivery conduit 12, such as in patient interface device 14. It should also be understood that exhaust vent 16 can have a wide variety of configurations depending on the desired manner in which gas is to be vented from pressure support system 2.

The present concept also contemplates that pressure support system 2 can be a two-limb system, having a delivery conduit and an exhaust conduit connected to patient 10. In a two-limb system (also referred to as a dual-limb system), the exhaust conduit carries exhaust gas from patient 10 and includes an exhaust valve at the end distal from patient 10. The exhaust valve in such an embodiment is typically actively controlled to maintain a desired level or pressure in the system, which is commonly known as positive end expiratory pressure (PEEP).

Furthermore, in the illustrated exemplary embodiment shown in FIG. 1, patient interface 14 is a nasal/oral mask. It is to be understood, however, that patient interface 14 can include a nasal mask, nasal pillows, a tracheal tube, an endotracheal tube, or any other device that provides a suitable gas flow communicating function. Also, for purposes of the present invention, the phrase "patient interface" can include delivery conduit 12 and any other structures that couple the source of pressurized breathing gas to patient 10.

In the illustrated embodiment, pressure support system 2 includes a pressure controller in the form of a valve 18 provided in internal delivery conduit 20 provided in a housing of pressure support device 4. Valve 18 controls the pressure of the flow of breathing gas from airflow generator 6 that is delivered to patient 10. For present purposes, airflow generator 6 and valve 18 are collectively referred to as a pressure generating system because they act in concert to generate and control the pressure and/or flow of gas delivered to patient 10. However, it should be apparent that other techniques for controlling the pressure of the gas delivered to patient 10, such as varying the blower speed of airflow generator 6, either alone or in combination with a pressure control valve, are contemplated by the present invention. Thus, valve 18 is optional depending on the technique used to control the pressure of the flow of breathing gas delivered to patient 10. If valve 18 is eliminated, the pressure generating system corresponds to airflow generator 6 alone, and the pressure of gas in the patient circuit is controlled, for example, by controlling the motor speed of airflow generator 6.

Pressure support system 2 further includes a flow sensor 22 that measures the flow of the breathing gas within delivery conduit 20 and delivery conduit 12. In the particular embodiment shown in FIG. 1, flow sensor 22 is interposed in line with delivery conduits 20 and 12, most preferably downstream of valve 18. Pressure support system 2 additionally includes a pressure sensor 27 that detects the pressure of the pressurized fluid in delivery conduit 20. While the point at which the flow is measured by flow sensor 22 and the pressure is measured by pressure sensor 27 are illustrated as being within pressure support device 4, it is to be understood that the location at which the actual flow and pressure measurements are taken may be anywhere along delivery conduits 20 or 12. The flow of breathing gas measured by flow sensor 22 and the pressure detected by pressure sensor 27 are provided to processing unit 24 to determine the flow of gas at patient 10 ($Q_{PATIENT}$).

Techniques for calculating $Q_{PATIENT}$ are well known, and take into consideration the pressure drop of the patient circuit, known leaks from the system, i.e., the intentional exhausting of gas from the circuit as indicated by arrow E in FIG. 1, and unknown leaks from the system, such as leaks at the mask/patient interface. The present invention contemplates using any known or hereafter developed technique for calculating leak flow, and using this determination in calculating $Q_{PATIENT}$ using measured flow and pressure. Examples of such techniques are taught by U.S. Pat. Nos. 5,148,802; 5,313,937; 5,433,193; 5,632,269; 5,803,065; 6,029,664; 6,539,940; 6,626,175; and 7,011,091, the contents of each of which are incorporated by reference into the present invention.

Of course, other techniques for measuring the respiratory flow of patient 10 are contemplated by the present invention, such as, without limitation, measuring the flow directly at patient 10 or at other locations along delivery conduit 12, measuring patient flow based on the operation of gas flow generator 6, and measuring patient flow using a flow sensor upstream of valve 18.

An input/output device 26 is provided for setting various parameters used by pressure support system 2, as well as for displaying and outputting information and data to a user, such as a clinician or caregiver.

Pressure support system 2 further includes a temperature sensor 28 that measure a temperature of the breathing gas provided to patient 10. Temperature sensor 28 may be included in or proximate to patient interface device 14 to measure the temperature of the breathing gas at patient 10. However, it will be appreciated that temperature sensor 28 or may be located elsewhere, such as in pressure support device 4 or conduit 12, without departing from the scope of the disclosed concept. It will also be appreciated that multiple temperature sensors 28 may be provided without departing from the scope of the disclosed concept.

Pressure support system 2 additionally includes a temperature conditioning unit 29. Temperature conditioning unit 29 is structured to adjust the temperature of breathing gas provided to patient 10. In some exemplary embodiments, temperature conditioning unit 29 may be a heating unit that is structured to heat the breathing gas provided to patient 10.

For example and without limitation, temperature conditioning unit 29 may include resistive heating elements that extend along conduit 12. Passing power through the resistive heating elements causes them to heat up, and thus heat up the breathing gas provided to patient 10 through conduit 12. However, it will be appreciated that other types of heating units structured to heat breathing gas provided to patient 10 may be used without departing from the scope of the disclosed concept. In some exemplary embodiments of the disclosed concept, temperature conditioning unit 29 may be structured to cool the breathing gas provided to patient 10. For example, in some environments, the ambient air temperature may be higher than what is comfortable for patient 10, so cooling the breathing gas is beneficial. In some exemplary embodiments, temperature conditioning unit 29 may be structured to selectively heat and cool breathing gas provided to patient 10.

Processing unit 24 is structured to estimate a CBT of patient 10 for selected times of day based on one or more inputs and to control temperature conditioning unit 29 to adjust the temperature of breathing gas provided to patient 10 at the selected times of day based on the estimated CBTs of patient 10 at the selected times of day. For example, a change in CBTs between selected times may be determined and the temperature of the breathing gas may be adjusted by the same amount as the change in CBT between the selected times. For example and without limitation, processing unit 24 may estimate that patient's 10 CBT will drop 0.25° C. per hour between 10 PM and 2 AM. In response, processing unit 24 may control temperature conditioning unit 29 to reduce the temperature of breathing gas provided to patient 10 by 0.25° C. per hour between 10 PM and 2 AM to match the estimated drop in patient's 10 CBT.

It will be appreciated that the selected times of day that processing unit 24 estimates patient's 10 CBT may be any amount of times up to and including a continuous estimation of patient's CBT. The selected times may be during a target period of day or over a full 24-hour period. It will also be appreciated that processing unit 24 may control temperature adjusting unit 29 to adjust the temperature of breathing gas provided to patient 10 based on the estimated CBT at any frequency up to and including continuously. It will also be appreciated that the temperature resolutions of the estimated CBT and temperature conditioning unit 29 (i.e., the smallest changes in temperatures) may be any amounts without departing from the scope of the disclosed concept. Processing unit 24 may use an output from temperature sensor 28 to ensure that the targeted temperature of breathing gas provided to patient 10 has been reached.

In the exemplary embodiment shown in FIG. 2, processing unit 24 is included in pressure support device 4. However, it will be appreciated that processing unit 24 may be located outside of pressure support device 24, such as in a server or other external computing device, or it may be distributed between pressure support device 4 and one or more external devices. For example, processing unit 24 may be distributed so as to include components to control temperature conditioning unit 29 inside pressure support device 29 and components to estimate the CBT of patient 10 inside an external device.

Processing unit 24 estimates patient's 10 CBT at selected times based on one or more inputs. Some examples of inputs are described in conjunction with FIG. 3.

Figure 3:
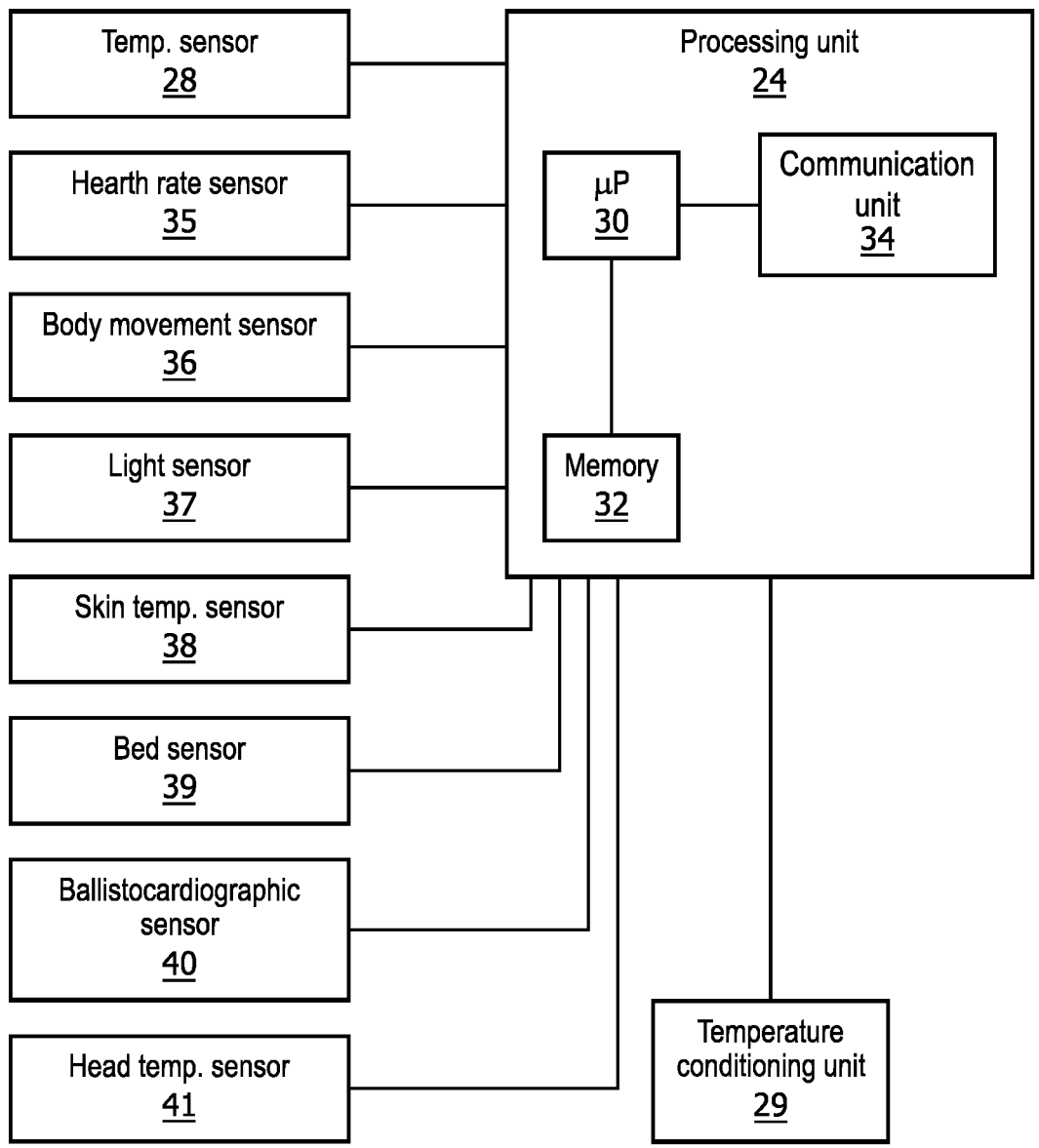
FIG. 3 is a schematic diagram of a portion of a pressure support system according to an exemplary embodiment of the disclosed concept.

FIG. 3 is a schematic diagram of a portion of pressure support system 2 in accordance with an exemplary embodiment of the disclosed concept. Processing unit 24 in accordance with an exemplary embodiment of the disclosed concept is shown in more detail in FIG. 3.

Processing unit 24 includes a processor 30, a memory 32, and a communication unit 34. Processor 30 may form all or part of a processing portion which may be, for example, a microprocessor, a microcontroller or some other suitable processing device. Memory 32 may form all or part of a memory portion that may be internal to the processing portion or operatively coupled to the processing portion and provide a storage medium for data and software executable by the processing portion for implementing functionality of processing unit 23 and controlling the operation of pressure support system 2. Memory 32 can be any of one or more of a variety of types of internal and/or external storage media such as, without limitation, RAM, ROM, EPROM(s), EEPROM(s), FLASH, and the like that provide a storage register, i.e., a machine readable medium, for data storage such as in the fashion of an internal storage area of a computer, and can be volatile memory or nonvolatile memory.

Communication unit 34 may provide for communication between processing unit 24 and other components of pressure support device 4, components of the patient circuit, or other external devices. For example and without limitation, communication unit 34 may facilitate communication with various sensors such as temperature sensor 29. Communication unit 34 may also facilitate communication with external devices. For example and without limitation, communication unit 34 may facilitate communication with electronic devices such as a phone, tablet, computer, or other devices directly or via a network. Communication facilitated by communication unit 34 may allow processing unit 24 to send and/or receive data from the component or device it communicates with.

The state of the circadian clock cannot be assessed directly in humans and usually one relies on indirect measures that are closely coupled to the activity of the circadian clock itself. Thermoregulation in general, and CBT in particular, is closely linked with the circadian rhythm, but it is difficult to accurately estimate comfortably. Measurements usually rely on ingestible or rectal thermometers.

Another marker of the phase of the circadian rhythm is the melatonin level, which is mainly affected by exposure to bright light. Given its relative resilience to masking effects, the dim light melatonin onset (DLMO) is the most practical indicator of circadian phase. However, it relies on the measurement of the level of melatonin in repeated saliva samples. This is impractical in home settings and for continued use. Other characteristics of patient 10 can be monitored to estimate the circadian rhythm of patient 10. As the circadian rhythm is closely linked with CBT, the estimated circadian rhythm of patient 10 can be used to estimate the CBT of the patient at selected times of day.

Heart rate variability is one characteristic that can be used to estimate the circadian rhythm of patient 10. For example, the heart rate of patient 10 drops during a sleep phase. A heart rate sensor 35 may be used to monitor the heart rate of patient 10. Heart rate sensor 25 may be, for example and without limitation, a wrist worn photoplethysmogram (PPG) or other type of cardiac sensor. Heart rate sensor 35 may sense the heart rate of patient 10 over a period of days and, from the sensed heart rate, processing unit 24 may estimate the sleep phase of patient 10. From the estimate sleep phase, processing unit 24 may estimate the circadian rhythm and CBT of patient 10.

Body movements are another characteristic that can be used to estimate the circadian rhythm of patient 10. During the sleep phase of patient 10, patient's 10 body moves little to none. A body movement sensor 36, such as a wristband, watch, or other device worn by patient 10, may be used to detect movement of patient's 10 body. Body movement sensing is also sometime referred to as actigraphy. Body movement sensor 36 may sense the body movement of patient 10 over a period of days and, from the sensed body movement, processing unit 24 may estimate the circadian rhythm and CBT of patient 10.

Light level exposure is another characteristic that can be used to estimate the circadian rhythm of patient 10. For example, sensing when patient 10 is in a dark environment (e.g., a darkened bedroom) can be used to estimate when patient 10 is in the sleep phase. A light sensor 37 may be used to sense when patient 10 is in a dark environment. For example, light sensor 37 may be, or may be integrated into a wearable device such as a wristband or watch. Light sensor 37 may sense patient's 10 light exposure over a period of days and, from the sensed light exposure, processing unit 24 may estimate the circadian rhythm and CBT of patient 10.

Distal skin temperature is another characteristic that can be used to estimate the circadian rhythm of patient 10. For example, the temperature of a distal region of patient's 10 body, such as in the area of the hands or feet, can be used to estimate when patient 10 is in the sleep phase. Patient's 10 distal skin temperature rises before patient 10 enters the sleep phase and CBT drops. A skin temperature sensor 38, such as a wristband sensor worn by patient 10, may be used to sense a distal skin temperature of patient 10 over a period of days and, from the sensed distal temperature, processing unit 24 may estimate the circadian rhythm and CBT of patient 10.

Presence/absence of patient 10 in bed is another characteristic that can be used to estimate the circadian rhythm of patient 10. For example, the times patient 10 is present in bed can be used estimate the sleep phase of patient 10. A bed sensor 39, such as a weight sensor located under a mattress or any other type of sensor suitable for sensing the presence/absence of patient 10 in bed, may be used sense patient's 10 presence/absence in bed over a period of days and, from the sensed presence/absence in bed, processing unit 24 may estimate the circadian rhythm and CBT of patient 10.

In some exemplary embodiments, a ballistocardiographic sensor 40 may be placed on or under patient's 10 mattress to measure patient's 10 heart rate while patient 10 is in bed. As described above, patient's 10 heart rate drops when patient 10 enters the sleep phase. Processing unit 24 may estimate circadian rhythm and CBT of patient 10 from an output of ballistocardiographic sensor 40.

In some exemplary embodiments, processing unit 24 estimates the CBT of patient 10 based on a sensed temperature of patient's 10 head. For example, a head temperature sensor 41 may be used to sense a temperature in the area of patient's 10 head. Head temperature sensor 41 may be integrated into a component of pressure support system 2 such as a mask strap that crosses the forehead of patient 10. Based on the sensed temperature of patient's 10 head, processing unit 24 may estimate a CBT of patient 10.

Outputs of any of sensors 35-41 may be used as inputs to processing unit 24 for estimating the CBT of patient 10 at selected times of day. It will be appreciated that FIG. 3 only illustrates examples of different types of sensors that may be used as inputs to processing unit 24. One or a subset of sensors 35-41 may be used as inputs to processing unit 24 for estimating the CBT of patient 10 with the rest of sensors 35-41 being omitted without departing from the scope of the disclosed concept. It will also be appreciated that sensors 35-41 are just example and other types of sensors may be employed without departing from the scope of the disclosed concept. Sensors 35-41 sense characteristics of patient 10 that are correlated with the CBT of patient 10. It will be appreciated that processing unit 24 may receive inputs from any other type of sensor that senses a characteristic of patient 10 correlated with the CBT of patient 10 without departing from the scope of the disclosed concept.

Sensors 35-41 may be directly connected to processing unit 24 via a direct connection to pressure support device 4 or sensors 35-41 may be separate from processing unit 24 and periodically connect to processing unit 24 to provide it with sensed data via one or more intermediate devices. For example, in the case where heart rate sensor 35 is a wristband worn by patient 10, heart rate sensor 35 may connect to a device such as a phone or tablet which may in turn connect to processing unit 24 and provide it with sensed data. As another example, bed sensor 39 may be directly connected to processing unit 24 via a connection to pressure support device 4, as bed sensor 39 can be expected to remain in patient's 10 bed by pressure support device 4.

In addition to or in alternative to inputs from one or more of sensors 35-41, processing unit 24 unit may receive profile information as an input used to estimate the CBT of patient 10 at selected times of day. The profile information may include, for example and without limitation, patient's 10 gender, age, or personal preferences. The profile information may be entered into an external device, such as a phone, tablet, or computer, and be communicated to processing unit 24.

Figure 4:
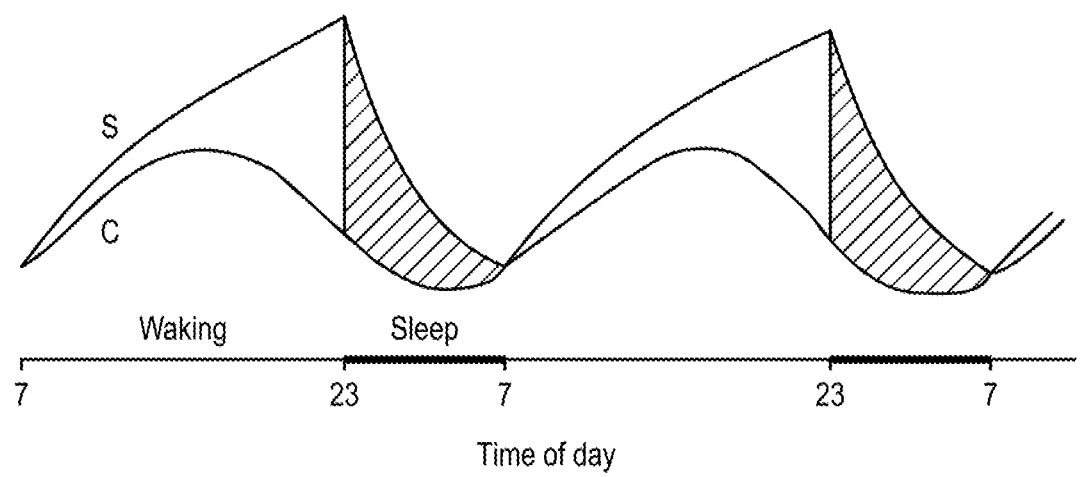
FIG. 4 is a graph showing a two-process model of alertness.

FIG. 4 is a graph showing a two-process model of alertness. FIG. 4 illustrates the interaction between the process S (homeostatic sleep pressure), process C (circadian rhythm), and the periods of wakefulness and sleep. As shown in FIG. 4, the sleep phase occurs during approximately the same points in the circadian rhythm each day. Based on the correlation between the sleep phase and the circadian rhythm, an estimate of the sleep phase can be used to estimate the circadian rhythm of patient 10 and, thus, the CBT of patient 10 can be estimated.

Figure 5:
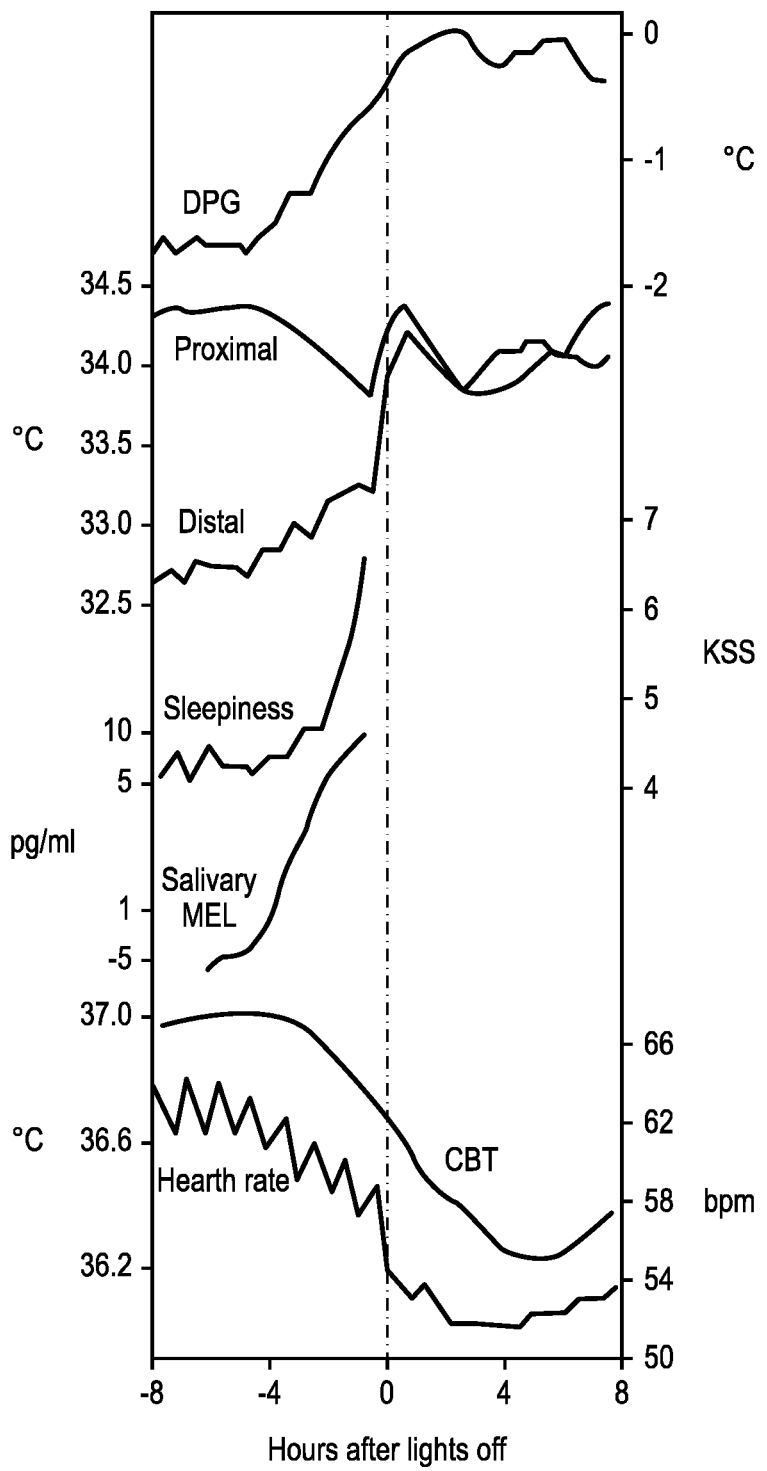
FIG. 5 is a graph showing the correlation of CBT and various characteristics over a period of time.

FIG. 5 is a graph showing the correlation of CBT and various characteristics over a period of time centered around when lights are turned off (i.e., approximately when a patient goes to sleep). The top portion of FIG. 5 shows distal proximal gradient (i.e., a difference between distal and proximal temperature of a patient), proximal temperature, and distal temperature of a patient in units of degrees Celsius. The middle portion of FIG. 5 shows sleepiness of a patient on the Karolinska Sleepiness Scale and salivary melatonin level of a patient in units of picograms per milliliter. The bottom portion of FIG. 5 shows CBT in units of degrees Celsius and heart rate of a patient in units of beats per minute. As can be seen from FIG. 5, the various characteristics show features leading up to or during the sleep phase where CBT drops. As such, these characteristics are correlated with the CBT during the sleep phase and can be used to estimate the CBT during the sleep phase.

Figure 6:
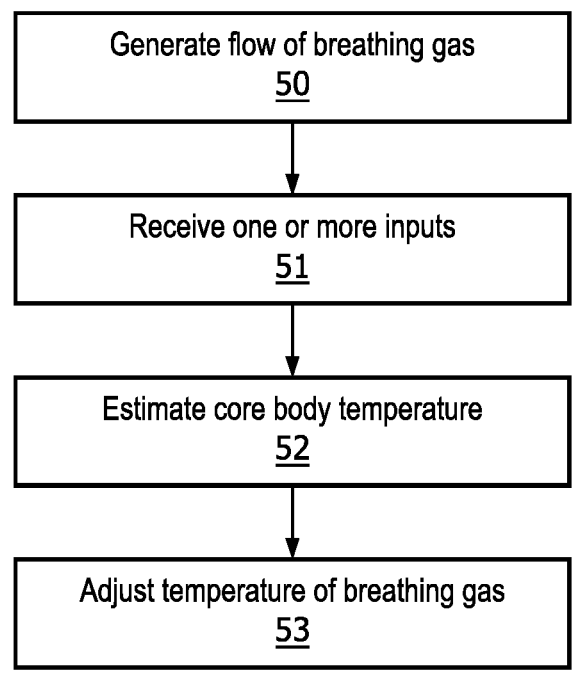
FIG. 6 is a flowchart of a method of providing pressure support therapy to a patient according to an exemplary embodiment of the disclosed concept.

FIG. 6 is a flowchart of a method of providing pressure support therapy to a patient according to an exemplary embodiment of the disclosed concept. The method may be implemented, for example and without limitation, in pressure support system 2 shown in FIGS. 2 and 3 and will be described in relation to pressure support system 2 shown in FIGS. 2 and 3. However, it will be appreciated that the method may be implemented in other types of pressure support systems without departing from the scope of the disclosed concept.

The method begins at 50 wherein a flow of breathing gas to be provided to a patient is generated. The flow of breathing gas may be generated, for example, by airflow generator 6, or other devices capable of generating airflow. At 51, one or more inputs are received. The one or more inputs may be received by processing unit 24 or other similar devices. At 52, the CBT of patient 10 is estimated for selected times of day based on the received inputs. The inputs may be, for example and without limitation, inputs from sensors 35-41, profile information of patient 10, or any other input of a characteristic of patient 10 correlated with the circadian rhythm of the patient. At 53, the temperature of the breathing gas provided to patient 10 is adjusted based on the estimated CBTs. For example, a change in CBTs between selected times may be determined and the temperature of the breathing gas may be adjusted by the same amount as the change in CBT between the selected times. The temperature may be adjusted by temperature conditioning unit 29 or similar devices under control of processing unit 24 or similar devices.

It is contemplated that aspects of the disclosed concept can be embodied as computer readable codes on a tangible computer readable recording medium. The computer readable recording medium is any data storage device that can store data which can be thereafter read by a computer system. Examples of the computer readable recording medium include read-only memory (ROM), random-access memory (RAM), CD-ROMs, magnetic tapes, floppy disks, and optical data storage devices.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A pressure support system for providing pressure support therapy to a patient, the pressure support device comprising:
    an airflow generator structured to generate a flow of breathing gas to the patient;
    a temperature conditioning unit structured to adjust a temperature of the breathing gas provided to the patient; and
    a processing unit structured to estimate a core body temperature of the patient for selected times of day based on one or more inputs and to control the temperature conditioning unit to adjust temperature of the breathing gas provided to the patient at the selected times of day based on the estimated core body temperatures of the patient, wherein the one or more inputs comprise inputs selected from the group consisting of (i) one or more sensors configured to detect a patient characteristic for use in estimating a circadian rhythm and correlated with the core body temperature of the patient for the selected times of day, (ii) profile information of the patient for use in estimating the core body temperature of the patient for the selected times of day, and (iii) any other input of a characteristic of the patient correlated with the circadian rhythm and correlated with the core body temperature of the patient for the selected times of day.

2. The pressure support system of claim 1, wherein the processing unit is structured to determine a change in estimated core body temperatures of the patient between selected times of day and to control the temperature conditioning unit to adjust the temperature of the breathing gas provided to the patient to by the same amount as the change in estimated core body temperatures of the patient between the selected times of day.

3. The pressure support system of claim 1, wherein the one or more inputs comprises the profile information of the patient.

4. The pressure support system of claim 3, wherein the profile information includes at least one of gender, age, and personal preferences of the patient.

5. The pressure support system of claim 1, wherein the one or more inputs comprises inputs from the one or more sensors.

6. The pressure support system of claim 5, wherein the one or more sensors are structured to sense a characteristic of the patient correlated with the circadian rhythm of the patient.

7. The pressure support system of claim 6, wherein the one or more sensors include at least one of a heart rate sensor, a body movement sensor, a light sensor, and a distal skin temperature sensor.

8. The pressure support system of claim 6, wherein the one or more sensors include at least one of a bed sensor and a ballistocardiographic sensor.

9. The pressure support system of claim 5, wherein the one or more sensors include a head temperature sensor structured to sense a temperature at the patient's head.

10. A method of providing pressure support therapy to a patient, the method comprising:
    generating, via an airflow generator, a flow of breathing gas to the patient;
    receiving, via a processing unit, one or more inputs;
    estimating, via the processing unit, a core body temperature of the patient for selected times of day based on the one or more inputs, wherein the one or more inputs comprise inputs selected from the group consisting of (i) one or more sensors configured to detect a patient characteristic for use in estimating a circadian rhythm and correlated with the core body temperature of the patient for the selected times of day, (ii) profile information of the patient for use in estimating the core body temperature of the patient for the selected times of day, and (iii) any other input of a characteristic of the patient correlated with the circadian rhythm and correlated with the core body temperature of the patient for the selected times of day; and
    adjusting, via a temperature conditioning unit, a temperature of the breathing gas provided to the patient at the selected times of day based on the estimated core body temperatures of the patient.

11. The method of claim 10, further comprising:
determining a change in estimated core body temperatures of the patient between selected times of day; and
adjusting the temperature of the breathing gas provided to the patient by the same amount as the change in estimated core body temperatures of the patient between the selected times of day.

12. The method of claim 10, wherein the one or more inputs comprises the profile information of the patient.

13. The method of claim 12, wherein the profile information includes at least one of gender, age, and personal preferences of the patient.

14. The method of claim 10, wherein the one or more inputs comprises inputs from the one or more sensors.

15. The method of claim 14, wherein the one or more sensors are structured to sense a characteristic of the patient correlated with the circadian rhythm of the patient.

16. The method of claim 15, wherein the one or more sensors include at least one of a heart rate sensor, a body movement sensor, a light sensor, and a distal skin temperature sensor.

17. The method of claim 15, wherein the one or more sensors include at least one of a bed sensor and a ballistocardiographic sensor.

18. The method of claim 14, wherein the one or more sensors include a head temperature sensor structured to sense a temperature at the patient's head.

19. A non-transitory computer readable medium storing one or more programs, including instructions, which when executed by a computer, causes the computer to perform a method of providing pressure support therapy to a patient, the method comprising:
generating a flow of breathing gas to the patient;
receiving one or more inputs;
estimating a core body temperature of the patient for selected times of day based on the one or more inputs; wherein the one or more inputs comprise inputs selected from the group consisting of (i) one or more sensors configured to detect a patient characteristic for use in estimating a circadian rhythm and correlated with the core body temperature of the patient for the selected times of day, (ii) profile information of the patient for use in estimating the core body temperature of the patient for the selected times of day, and (iii) any other input of a characteristic of the patient correlated with the circadian rhythm and correlated with the core body temperature of the patient for the selected times of day; and
adjusting a temperature of the breathing gas provided to the patient at the selected times of day based on the estimated core body temperatures of the patient.

20. The non-transitory computer readable medium of claim 19, wherein the method further comprises:
determining a change in estimated core body temperatures of the patient between selected times of day; and
adjusting the temperature of the breathing gas provided to the patient by the same amount as the change in estimated core body temperatures of the patient between the selected times of day.

\* \* \* \* \*